US00PP32106P3

(12) United States Plant Patent
van den Haak

(10) Patent No.: US PP32,106 P3
(45) Date of Patent: Aug. 18, 2020

(54) ***HEUCHERA* PLANT NAMED 'IFHEPR'**

(50) Latin Name: *Heuchera hybrida*
Varietal Denomination: IFHEPR

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 16/501,902

(22) Filed: Jul. 1, 2019

(65) Prior Publication Data

US 2020/0022297 P1 Jan. 16, 2020

Related U.S. Application Data

(60) Provisional application No. 62/764,038, filed on Jul. 13, 2018.

(51) Int. Cl.
*A01H 5/12* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC . A01H 5/02; A01H 5/12; A01H 5/025; A01H 6/80
See application file for complete search history.

*Primary Examiner* — June Hwu
(74) *Attorney, Agent, or Firm* — C. A. Whealy

(57) ABSTRACT

A new and distinct cultivar of *Heuchera* plant named 'IFHEPR', characterized by its compact and uniformly mounded plant habit; relatively rapid growth rate; densely foliated and bushy appearance; greyed red-colored leaves; long flowering period; numerous inflorescences with sterile light purple-colored flowers; and good garden performance and winter hardiness.

2 Drawing Sheets

Botanical designation: *Heuchera hybrida.*
Cultivar denomination: 'IFHEPR'.

BACKGROUND OF THE INVENTION

The present invention relates to a new and distinct *Heuchera* plant, botanically known as *Heuchera hybrida*, typically grown as a landscape *Heuchera* and hereinafter referred to by the name 'IFHEPR'.

The new *Heuchera* plant is a product of a planned breeding program conducted by the Inventor in Andijk, The Netherlands. The objective of the breeding program is to create new compact *Heuchera* plants with attractive leaf and flower coloration and good garden performance.

The new *Heuchera* plant originated from a cross-pollination of *Heuchera hybrida* 'Crimson Curls', disclosed in U.S. Plant Pat. No. 13,729, as the female, or seed, parent with a proprietary selection of *Heuchera hybrida* identified as code number 083-09-C013, not patented, as the male, or pollen, parent in June, 2012. The new *Heuchera* plant was discovered and selected as a single plant from within the progeny of the stated cross-pollination in a controlled nursery environment in Andijk, The Netherlands in July, 2013.

Asexual reproduction of the new *Heuchera* plant by in vitro meristem culture in a controlled environment in Andijk, The Netherlands since September, 2016 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFHEPR'. These characteristics in combination distinguish 'IFHEPR' as a new and distinct *Heuchera* plant:

1. Compact and uniformly mounded plant habit.
2. Relatively rapid growth rate.
3. Densely foliated and bushy appearance.
4. Greyed red-colored leaves.
5. Long flowering period.
6. Numerous inflorescences with sterile light purple-colored flowers.
7. Good garden performance and winter hardiness.

Plants of the new *Heuchera* differ primarily from plants of the female parent, 'Crimson Curls', in leaf color as plants of the new *Heuchera* have greyed red-colored leaves whereas plants of 'Crimson Curls' have dark purple brown and crimson-colored leaves. In addition, leaf margins of plants of the new *Heuchera* are not as undulate as leaf margins of plants of 'Crimson Curls'.

Plants of the new *Heuchera* differ primarily from plants of the male parent selection in leaf color as plants of the new *Heuchera* have greyed red-colored leaves whereas plants of the male parent selection have red-colored leaves. In addition, leaf margins of plants of the new *Heuchera* are more undulate than leaf margins of plants of the male parent selection.

Plants of the new *Heuchera* can be compared to plants of *Heuchera hybrida* 'Paprika', disclosed in U.S. Plant Pat. No.

24,575. In side-by-side comparisons, plants of the new *Heuchera* differ primarily from plants of 'Paprika' in the following characteristics:

1. Plants of the new *Heuchera* are more compact and denser than plants of 'Paprika'.
2. Plants of the new *Heuchera* have greyed red-colored leaves whereas plants of 'Paprika' have peach to burgundy-colored leaves.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet is a side perspective view of a typical flowering plant of 'IFHEPR' grown in a container.

The photograph at the top of the second sheet is a close-up view of typical leaves of 'IFHEPR'.

The photograph at the bottom of the second sheet is a close-up view of a typical inflorescence of 'IFHEPR'.

DETAILED BOTANICAL DESCRIPTION

The aforementioned photographs and following observations, measurements and values describe plants grown during the summer with three plants in a 15-cm containers in an outdoor nursery in Heerhugowaard, The Netherlands and under cultural practices typical of commercial *Heuchera* production. During the production of the plants, day temperatures ranged from 10° C. to 25° C. and night temperatures ranged from 4° C. to 15° C. Plants were 18 weeks old when the photographs and the description were taken. In the following description, color references are made to The Royal Horticultural Society Colour Chart, 2015 Edition, except where general terms of ordinary dictionary significance are used.

Botanical classification: *Heuchera hybrida* 'IFHEPR'.

Parentage:

*Female, or seed, parent.*—*Heuchera hybrida* 'Crimson Curls', disclosed in U.S. Plant Pat. No. 13,729.

*Male, or pollen, parent.*—Proprietary selection of *Heuchera hybrida* identified as code number 083-09-C013, not patented.

Propagation:

*Type.*—By in vitro meristem culture.

*Time to initiate roots, summer.*—About ten days at temperatures about 22° C.

*Time to initiate roots, winter.*—About 15 days at temperatures about 20° C.

*Time to produce a rooted young plant, summer.*—About 42 days at temperatures about 20° C.

*Time to produce a rooted young plant, winter.*—About 50 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial; basal rosette plant habit with leaves developing from the base; densely foliated and dense and bushy appearance; compact and uniformly mounded plant habit; overall shape, flattened globular with upright inflorescences held above the foliar plane; moderately vigorous growth habit; moderate growth rate.

*Plant height, soil level to top of foliar plane.*—About 12.6 cm.

*Plant height, soil level to top of inflorescences.*—About 71 cm.

*Plant diameter or spread.*—About 33.1 cm.

Leaf description:

*Arrangement.*—Alternate in basal rosettes; simple.

*Length.*—About 8.5 cm.

*Width.*—About 8.1 cm.

*Shape.*—Broadly ovate to close to orbicular; palmately lobed.

*Apex.*—Obtuse with a small and short abruptly acute tip.

*Base.*—Hastate, lobes touching to slightly imbricate.

*Margin.*—About seven lobes per leaf; crenate with small and short abruptly acute tips; sinuses medium in depth and divergent; strongly undulate.

*Texture and luster, upper surface.*—Sparsely to moderately pubescent; slightly glossy.

*Texture and luster, lower surface.*—Venation, pubescent; moderately glossy.

*Venation pattern.*—Palmate; reticulate.

*Color.*—Developing leaves, upper surface: Close to 178A and 183C. Developing leaves, lower surface: Close to 187C. Fully expanded leaves, upper surface: Close to 147A tinged with close to 182B; venation, close to 148A and 148B. Fully expanded leaves, lower surface: Close to 187C; venation, close to N186C.

*Petioles.*—Length: About 11 cm. Diameter: About 2.5 mm. Strength: Moderately strong. Texture and luster, upper and lower surfaces: Densely pubescent; glossy. Color, upper surface: Close to 200B slightly tinged with close to N186C. Color, lower surface: Close to between N186C and 200B.

*Stipules.*—Quantity and arrangement: One at the base of each leaf. Length: About 1 cm. Width: About 4 mm. Shape: Lanceolate with acute apex. Color, upper and lower surfaces: Close to N79D.

Flower description:

*Flower type and flowering habit.*—Single campanulate flowers arranged on axillary compound spikes; each spike with about 250 flowers; about 2,500 flowers develop per plant during the flowering season; flowers face outwardly to slightly nodding.

*Fragrance.*—None detected.

*Time of flowering.*—Plants flower continuously from the spring into the summer in The Netherlands; plants begin flowering about four months after planting.

*Inflorescence longevity.*—Individual flowers last about a week on the plant; flowers not persistent.

*Inflorescence length.*—About 41.4 cm.

*Inflorescence width.*—About 9.2 cm.

*Flower diameter.*—About 7 mm.

*Flower depth (height).*—About 8 mm.

*Flower buds.*—Height: About 4 mm. Diameter: About 2.5 mm. Shape: Obovate. Texture and luster: Densely pubescent; matte. Color: Close to 64A.

*Petals.*—Quantity and arrangement: Five petals in a single whorl. Length: About 4 mm. Width: About 1 mm. Shape: Oblanceolate. Apex: Acute. Base: Narrowly attenuate. Margin: Entire. Texture and luster, upper surface: Smooth, glabrous; matte. Texture and luster, lower surface: Sparsely pubescent; matte. Color: When opening, upper and lower surfaces: Close to NN155D. Fully opened, upper and lower surfaces: Close to NN155D; venation, close to NN155D; color does not change with development.

*Sepals.*—Quantity and arrangement: Five sepals in a single whorl; lower 60% fused. Length: About 6.5 mm. Width: About 2 mm. Shape: Oblong. Apex: Obtuse. Margin: Entire. Texture and luster, upper surface: Smooth, glabrous; matte. Texture and luster, lower surface: Densely pubescent; matte. Color: When opening, upper surface: Close to 76B; towards the margins, close to 79D. When opening, lower surface: Close to 64C. Fully opened, upper surface: Close to 76B; towards the margins, close to 76D; distally, tinged with close to 146D. Fully opened, lower surface: Close to 70B; towards the margins, close to N155B.

*Peduncles.*—Length: About 69.2 cm. Diameter: About 2.5 mm. Strength: Moderately strong. Aspect: Erect to about 70° from vertical. Texture and luster: Moderately to densely pubescent; glossy. Color: Close to between N186C and 200A.

*Pedicels.*—Length: About 4.5 mm. Diameter: About 0.5 mm. Strength: Moderately strong. Aspect: About 45° from peduncle axis. Texture and luster: Densely pubescent; slightly glossy. Color: Close to 183A.

*Reproductive organs.*—Androecium: Stamen number: Five per flower. Filament length: About 3.5 mm. Filament color: Close to NN155D. Anther size: About 0.5 mm by 0.5 mm. Anther shape: Deltoid. Anther color: Close to 168C. Amount of pollen: Moderate to abundant. Pollen color: Close to 10B. Gynoecium: Pistil number: Two per flower. Pistil length: About 5 mm. Style length: About 4.75 mm. Style color: Close to between 155A and 161D. Stigma diameter: About 0.2 mm. Stigma shape: Club-shaped. Stigma color: Close to 164D. Ovary color: Close to 161D.

*Seeds and fruits.*—To date, seed and fruit development have not been observed on plants of the new *Heuchera.*

Pathogen & pest resistance: To date, plants of the new *Heuchera* have not been observed to be resistant to pathogens and pests common to *Heuchera* plants.

Garden performance: Plants of the new *Heuchera* have been observed to have good garden performance and to tolerate high temperatures about 35° C. and to be suitable for USDA Hardiness Zones 3 through 9.

It is claimed:

1. A new and distinct *Heuchera* plant named 'IFHEPR' as illustrated and described.

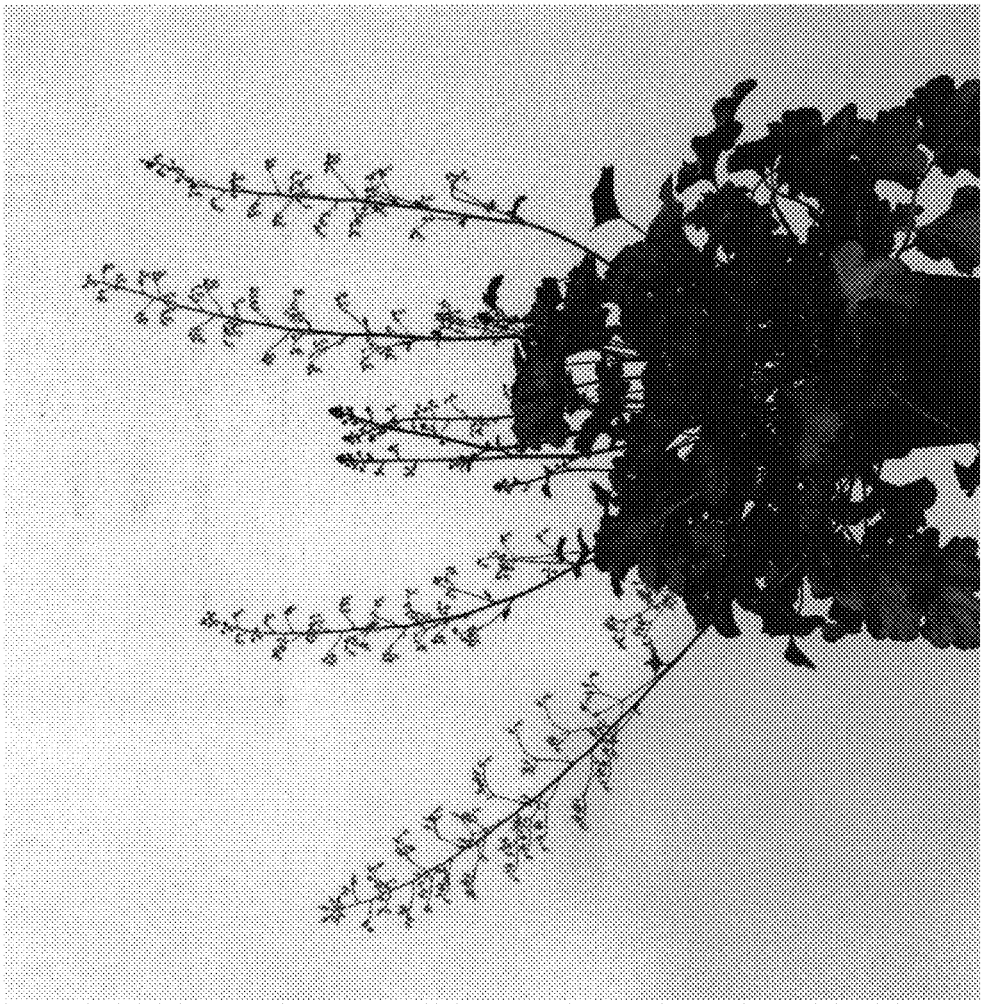

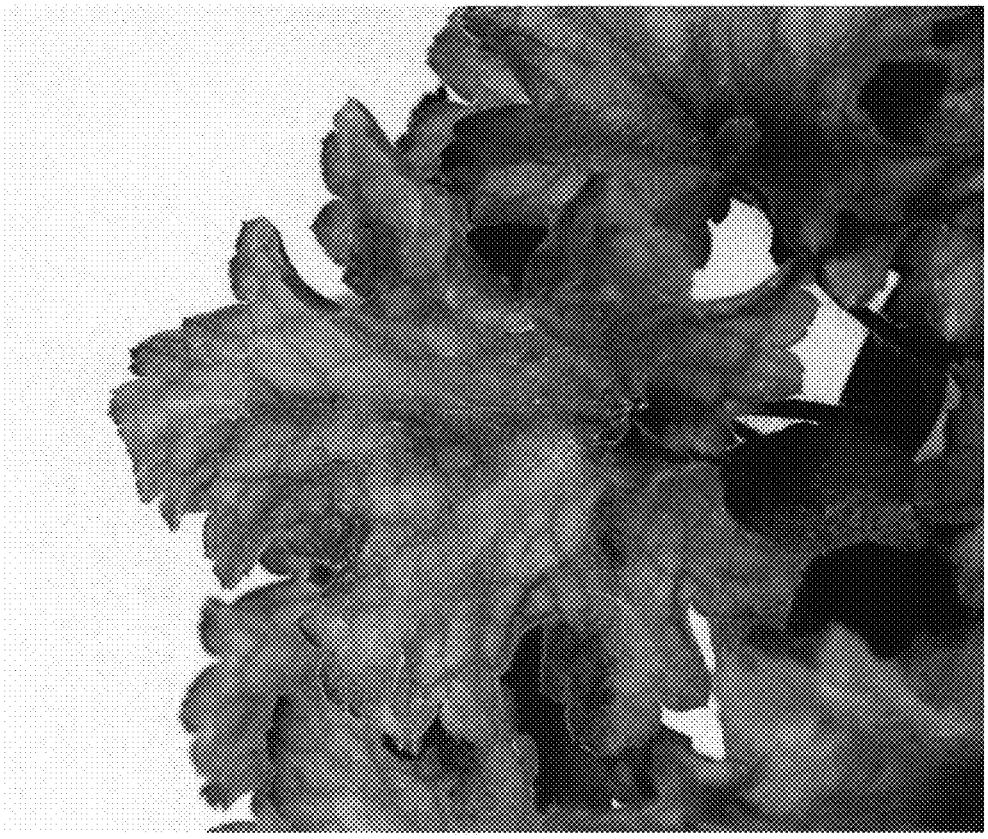
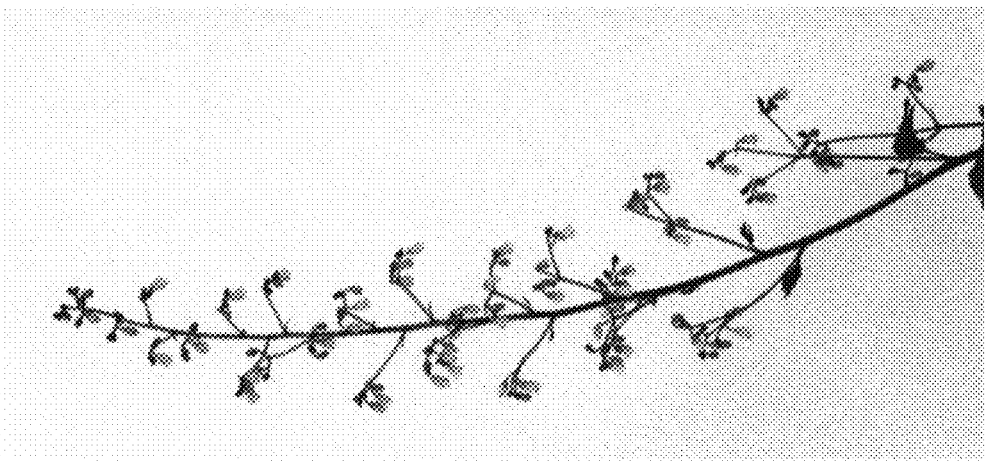

* * * * *